US006806478B1

(12) United States Patent
Hatfield

(10) Patent No.: US 6,806,478 B1
(45) Date of Patent: Oct. 19, 2004

(54) AUTHENTICATION SYSTEM AND METHODOLOGY

(75) Inventor: Galen R. Hatfield, Ellicott City, MD (US)

(73) Assignee: Cryovac, Inc., Duncan, SC (US)

(*) Notice: Subject to any disclaimer, the term of this patent is extended or adjusted under 35 U.S.C. 154(b) by 0 days.

(21) Appl. No.: 09/268,892

(22) Filed: Mar. 16, 1999

(51) Int. Cl.[7] .................................................. A61N 5/00

(52) U.S. Cl. ................................ 250/492.1; 250/472.1; 250/482.1

(58) Field of Search ........................... 250/492.1, 472.1, 250/474.1, 482.1; 523/136; 325/364

(56) References Cited

U.S. PATENT DOCUMENTS

| | | | |
|---|---|---|---|
| 3,063,010 A | 11/1962 | Richardson | 325/364 |
| 3,899,677 A | 8/1975 | Hori et al. | |
| 4,056,729 A | 11/1977 | Collica et al. | |
| 4,143,274 A | 3/1979 | Apfel | |
| 4,466,942 A | 8/1984 | Rogers | |
| 4,652,763 A | 3/1987 | Nablo | |
| 4,668,714 A | 5/1987 | Morita et al. | 523/136 |
| 4,765,468 A | 8/1988 | Graham | |
| 5,066,863 A | 11/1991 | Hanisch et al. | 250/474.1 |
| 5,206,118 A | 4/1993 | Sidney et al. | |
| 5,451,505 A | 9/1995 | Dollinger | |
| 5,501,945 A | 3/1996 | Kanakkanatt | |
| 5,644,352 A * | 7/1997 | Chang et al. | 347/221 |

FOREIGN PATENT DOCUMENTS

| | | |
|---|---|---|
| FR | 1 303 278 | 1/1973 |
| FR | 2 402 681 | 4/1979 |
| GB | 835120 | 5/1960 |
| JP | 1-169387 | 7/1989 |
| WO | 94/16902 | 8/1994 |
| WO | 97/19763 | 6/1997 |
| WO | 98/06574 | 2/1998 |

OTHER PUBLICATIONS

ESR study of free radicals created by irradiation in some organic substances. (Nucl. Sci. Abstr. 1970. 24(17).

Mixed–Field dosimetry in a cyclotron–produced fast neutron radiotherapy beam with special emphasis on a newly developed alanine system (Inst. Nucl. Phys., Krakow, Pol.).

Free radical dosimetry by chemical readout (Div. Radiol. Prot., Bhabha At. Res. Cent., Bombay, 400 085 India).

Thin Film Alanine–Polyethylene dosimeter (Appl. Radiat. Isot. 44, 1993) pp. 41–45.

Alanine Dosimeters Using polymers as Binders (Appl. Radiat. Isot. 37, No. 6) pp. 517–520—1986.

Doeimetry by ESR Spectroscopy of Alanine (Appl. Radiat. Isot. 33) pp. 1101–1114—1982.

Use of Glucose Solutions in Cobalt–60 Gama Ray Dosimetry (Int. Journal of Applied Radiation . . . ) vol. 21 pp. 143–146.

* cited by examiner

*Primary Examiner*—Kiet T. Nguyen
(74) *Attorney, Agent, or Firm*—Daniel B. Ruble

(57) ABSTRACT

The present invention provides an authentication system and methodology in which an authenticating agent is used as a product marker to help determine the source of products. The authenticating agent includes a substance that forms free radicals upon irradiation. The spectroscopic response of the agent when in the free radical state provides a characteristic "fingerprint" associated with genuine goods, but lacking in other goods. The goods incorporating the marker may be readily identified and/or distinguished from similar goods originating from another source. Furthermore, when not in the activated state, the authenticating agent typically is not detectable, thus providing the advantage of not being readily identifiable by counterfeiters.

32 Claims, 5 Drawing Sheets

AUTHENTICATION SYSTEM AND METHODOLOGY

BACKGROUND INFORMATION

1. Field of the Invention

The present invention relates generally to an authentication system and methodology in which items incorporating an authenticating agent as a product marker can be used to confirm the source of the items. More specifically, the authenticating agent of the present invention forms detectable free radicals upon exposure to a suitable dosage of ionizing radiation. An item can be irradiated and then subjected to spectroscopic analysis in an easy, straightforward fashion to determine whether it incorporates the marker and therefore comes from a particular source.

2. Background of the Invention

Throughout history, extensive efforts have been undertaken by manufacturers of industrial and retail goods in attempts to ensure that their goods can be readily distinguished from the goods of others. Measures used in this effort have included the use of unique product markers. Such markers have been physically observable features placed on goods (e.g., holograms, microreplicated patterns, water marks, product codes, trademarks, trade dress, and the like) or chemical authenticating agents (e.g. fluorescent materials, special inks, dyes or the like) that have unique, detectable properties which often are hidden under normal conditions. See, e.g., U.S. Pat. No. 5,644,352 (Chang), as well as the documents cited therein, for a general discussion of product markers.

One reason that product markers are used is to distinguish genuine goods from counterfeit goods. Unfortunately, counterfeiters have been able to duplicate conventional product markers without too much effort or expense. A product marker provides poor protection against counterfeit goods if counterfeiters can easily misappropriate it. The manner in which counterfeiters have trafficked counterfeit CD-ROM discs is one example of how counterfeiters are able to duplicate markers and thereby circumvent conventional authentication approaches.

Recently, fluorescent compounds have been incorporated into products as latent product markers that can be activated on demand and then detected by visual inspection. Advantageously, these markers are hidden under normal conditions and become visible only when the compounds are exposed to the right kind of radiation, e.g., ultraviolet light. Counterfeiters may not even know that such markers are being used. Consequently, these fluorescent compounds have proven to be excellent product markers. However, to be functional, the compounds must be positioned carefully on a product or its packaging.

Thus, there continues to be a strong demand for an authentication scheme that is difficult for counterfeiters to duplicate and that does not limit marker placement to the surface of a marked product.

Thwarting counterfeiters is not the only reason that manufacturers may desire to mark their products with unique markers. Markers also can be used so that the source of products can be confirmed when the performance of the products, good or bad, becomes an issue. The need for such markers is particularly strong in markets in which products sold by different manufacturers legitimately look similar to each other. For example, plastic container closures such as screw-on beverage bottle caps typically look similar regardless of source. Such closures typically include liners that help provide a good seal when the closure is engaged on a container opening. A manufacturer of closures may purchase liners from more than one manufacturer. Thus, if the seal on some closures fails because of a faulty liner, it may be desirable to determine the manufacturer of the faulty liners. Since liners from different manufacturers look similar, this determination can be difficult.

In such instances, a unique product marker that allows the source of the products at issue to be identified with certainty can be highly desirable. In many of these instances, the marker preferably is hidden so that all of the products visually look the same to the customer, regardless of the manufacturer supplying the goods. Incorporating the marker into the product so as not to affect product performance or to be harmful to the user also is highly desirable.

SUMMARY OF THE INVENTION

The present invention provides an improved authentication system and methodology in which an authenticating agent is used as a product marker to help determine the source of products. The authenticating agent includes a substance that forms free radicals upon irradiation. The authenticating agents has a first, latent state that provides a first response to spectroscopic analysis and a second, activated state that provides a second, distinguishable response to spectroscopic analysis. The spectroscopic response of the marker when in the activated, free radical state provides a characteristic “fingerprint” associated with genuine goods, but lacking in other goods. Goods incorporating the marker thus may be readily identified and/or distinguished from similar goods originating from another source that lack the marker. Furthermore, because the authenticating agent can be incorporated into the goods in a latent state, it is not a separate, visually identifiable component of the package and is preferably not detectable in its first, latent state, even by spectroscopic means.

In one aspect, the present invention relates to a package including a product that is packaged, at least in part, by a packaging material. The packaging material incorporates an authenticating agent that includes a substance that forms detectable free radicals upon exposure to ionizing radiation. Since preferred methods of analysis do not involve the transmission or reflectance of light, the authenticating agent preferably and advantageously may be incorporated into either or both of the product(s) or packing material(s) without regard to the location, i.e., the agent need not be readily apparent to the unaided eye. In particularly preferred embodiments, the authenticating agent includes an amino acid such as alanine.

A package in accordance with the present invention can be subjected to spectroscopic analysis to determine authenticity or source. Thus, in another aspect, the present invention relates to a method of analyzing a sample to determine whether the sample contains an authenticating agent that forms free radicals upon exposure to ionizing radiation. The method involves irradiating the sample with ionizing radiation and then subjecting the irradiated sample to a spectroscopic analysis effective to provide a spectroscopically derived output indicative of the presence, if any, of free radicals. A determination of whether the sample contains the free radicals is made from information including the spectroscopically derived output of the sample.

In another aspect, the present invention relates to a method of making a package, in which an authenticating agent (as described above) is incorporated into a component of the package as a product marker. The authenticating agent is present in a manner such that the free radicals provide a characteristic spectral response when subjected to a spectroscopic analysis capable of detecting free radicals. The source of the package can be determined from the spectral response.

In yet another aspect, the present invention relates to an authenticating system. The system includes an authenticating agent including a substance that forms free radicals upon irradiation with ionizing radiation. The system further includes reference information derived from data including the spectroscopically derived output resulting from spectroscopic analysis of an irradiated reference sample, wherein the irradiated reference sample includes an amount of free radicals. Also provided is a source of ionizing radiation and a spectroscopic system effective to provide a spectroscopically derived output of a sample to be authenticated wherein the output is indicative of the presence, if any, of the free radicals in the sample to be authenticated.

To assist in understanding the description of the invention that follows, provided immediately below are certain definitions which apply hereinthroughout unless a contrary intention is explicitly indicated:

"free radical" means a molecular fragment having one or more unpaired electrons, wherein the fragment is formed by splitting a covalent bond;

"monomer" means a single, one unit molecule capable of combination with itself or other monomers to form oligomers or polymers;

"oligomer" means the polymerization product of 2 to 20 monomers;

"polymer" means the polymerization product of 21 or more monomers and is inclusive of homopolymers, copolymers, and interpolymers as well as blends and modifications thereof;

"mer unit" means that portion of a polymer derived from a single monomer; for example, a mer unit derived from ethylene has the general formula ($—CH_2CH_2—$);

"homopolymer" means a polymer consisting essentially of a single type of repeating mer unit;

"copolymer" means a polymer that includes mer units derived from two monomers and is inclusive of random, block, segmented, graft, etc., copolymers;

"interpolymer" means a polymer that includes mer units derived from at least two monomers and is inclusive of copolymers, terpolymers, tetrapolymers, and the like;

"(meth)acryl" means methacryl, acryl, and homologs thereof in which the substituent on the carbon in the alpha position relative to the carboxyl moiety may not only be hydrogen (acryl) or methyl (methacryl), but may also be lower alkyl or cycloalkyl or other suitable monovalent moieties;

"transverse direction" means that direction across a film and perpendicular to the longitudinal direction;

"free shrink" means the percent dimensional change, as measured by ASTM D 2732, in a 10 cm×10 cm specimen of film when it is subjected to heat;

as a verb, "laminate" means to affix or adhere (by means of, for example, adhesive bonding, pressure bonding, corona lamination, and the like) two or more separately made film articles to one another so as to form a multilayer structure, as a noun, "laminate" means a product produced by the affixing or adhering as just described;

"directly adhered," as applied to film layers, means adhesion of the subject film layer to the object film layer, without a tie layer, adhesive, or other layer therebetween.

"inner layer" means a layer of a film having each of its principal surfaces directly adhered to one other layer of the film;

"outer layer" means a layer of a film having less than both of its principal surfaces directly adhered to other layers of the film;

"barrier layer" means a film layer capable of excluding one or more gases (e.g., $O_2$);

"abuse layer" means an outer layer and/or an inner layer that resists abrasion, puncture, and other potential causes of reduction of package integrity and/or appearance quality;

"tie layer" means an inner layer having the primary purpose of providing interlayer adhesion to adjacent layers that include otherwise non-adhering polymers;

"bulk layer" means any layer which has the purpose of increasing the abuse resistance, toughness, modulus, etc., of a multilayer film and generally includes polymers that are inexpensive relative to other polymers in the film which provide some specific purpose unrelated to abuse resistance, modulus, etc.;

"comprising" is an open-ended term that means that the recited elements are only a part of the product, method or system and that the composition, product, method, system, or the like may include other elements not explicitly mentioned; and "seal layer" (or "sealing layer" or "heat seal layer" or "sealant layer") means (a) with respect to lap-type seals, one or more outer film layer(s) involved in the sealing of the film to itself (in some circumstances, as much as the outer 75 μm of a film can be involved in the sealing of the film to itself or another layer), another film layer of the same or another film, and/or another article which is not a film, or (b) with respect to fin-type seals, an inside film layer of a package, as well as supporting layers within 75 μm of the inside surface of the innermost layer, involved in the sealing of the film to itself, and as a noun, "seal" means a bond of a first region of a film surface to a second region of a film surface (or opposing film surfaces) created by heating (e.g., by means of a heated bar, hot air, infrared radiation, ultrasonic sealing, etc.) the regions (or surfaces) to at least their respective softening points so as to cause bonding between polymer chains.

DETAILED DESCRIPTION OF ILLUSTRATIVE EMBODIMENTS

Figure 1A:
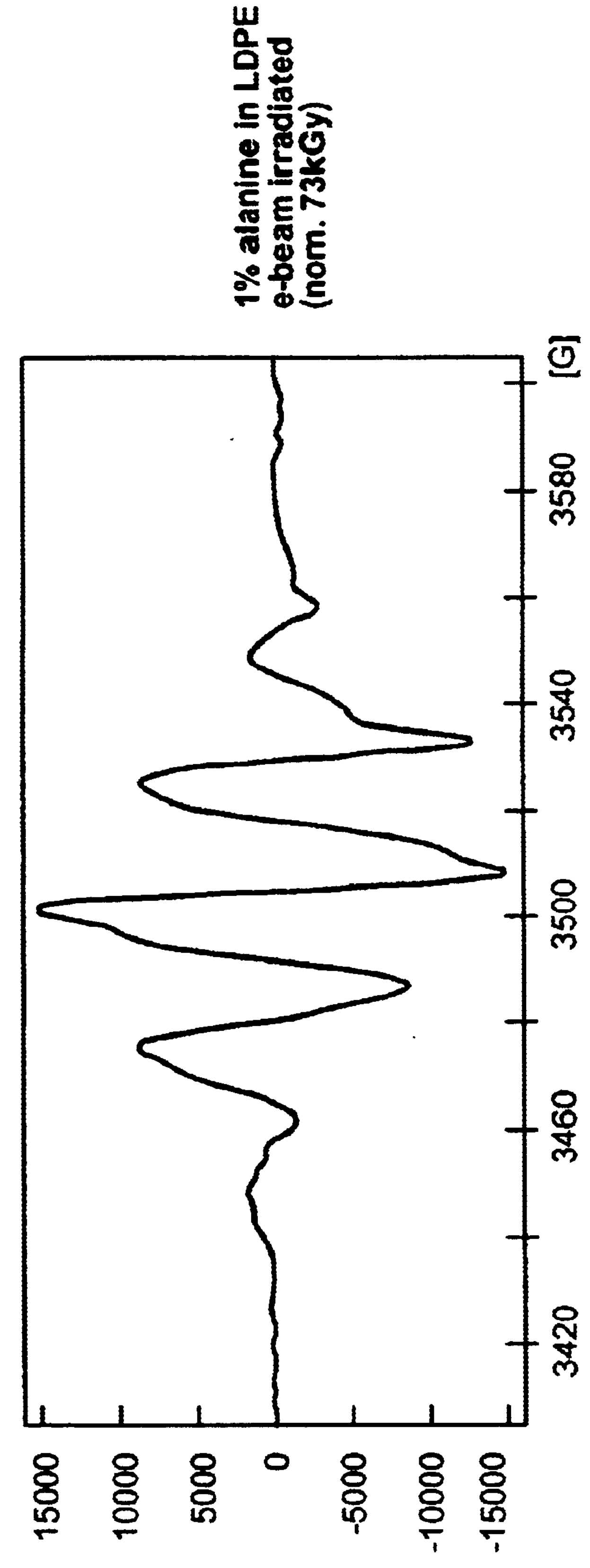
FIG. 1A is an electron spin resonance spectrum of a low density polyethylene (LDPE) film including 1% L-alanine that has been exposed to electron beam irradiation at a dose of 73 kGy.

The following embodiments of the present invention are not intended to be exhaustive or to limit the invention to the precise forms disclosed in the following detailed description. Rather the embodiments are chosen and described so that others skilled in the art may appreciate and understand the principles and practices of the present invention.

The present invention provides a package, a method of making a package, a method of analyzing a sample and an authentication system, wherein an authenticating agent is used to help determine the source of products. The spectroscopic response of the agent provides a characteristic response that is present in genuine goods while lacking in others. Goods incorporating such an agent are readily distinguished from similar goods. However, the agent is advantageously not generally a visually identifiable component of the package and thus not readily copied by counterfeiters.

Authenticating agents of the present invention provide unique, characteristic spectroscopic responses that vary depending upon how much agent is used, how many agents are used, the radiation dosage used to activate the agent(s), and the like. Accordingly, each unique authenticating agent formulation can provide a unique spectroscopic response characteristic of that particular formulation. Because each formulation of authenticating agents provides a unique spectroscopic response, the information that may be conveyed by the authenticating agents is not necessarily limited to information relating to the authenticity of a product. For instance, due to the fact that the authenticating agents generally are not visible to the unaided eye, the authenticating agents can be used to secretly convey a variety of information, such as source information; manufacturing date information; product, serial or model number information; warranty information; product features; or the like.

In some instances, a counterfeiter may be able to determine how to activate, detect, and identify the authenticating agent(s) utilized in a package or product of the present invention. The counterfeiter then could produce goods incorporating the marker in efforts to misappropriate the profits and/or goodwill of the authentic package manufacturer. To prevent this, manufacturers can take advantage of the ability of numerous authenticating agents to be combined, as well as the fact that each authenticating agent or combination provides a unique spectral response, to vary the formulation of the product marker from time to time. This can provide an additional layer of security to protect against counterfeit activity.

Advantageously, preferred authenticating agents generally retain their spectroscopic detectability even when mixed, blended, compounded or otherwise physically combined with almost all materials, whether solid or liquid. Thus, so long as the material(s) and the authenticating agent do not react with each other in a manner that degrades or destroys the spectroscopic detectability of the agent, and so long as the act of combining the material(s) and the authenticating agent does not involve processing conditions that affect the spectroscopically detectable characteristics of the agent, the authenticating agent may be incorporated into virtually any material chosen for use in the product or the packaging material of the authentic product. Examples of materials that may be advantageously used in the authentic packages of the present invention include heterogeneous or homogeneous blends, mixtures, solutions, composites, and the like, of organic and/or inorganic substances such as monomers, oligomers, polymers, wood, ceramic materials, metals (including pure metals, metal alloys, intermetallic compositions, and the like), paperboard, chipboard, cardboard and the like. Clearly, the choice of authenticating agent is not particularly limited by the materials of the product or packaging material of the package of the present invention.

Preferred authenticating agents of the present invention include substances that have a first, latent state that provides a first spectral response to spectroscopic analysis and a second, activated state that provides a second, distinguishable spectral response to spectroscopic analysis. Particularly preferred substances to be used as a authenticating agents are those that are "truly latent", i.e., those that have a first, latent state which provides no more than a negligible response to spectroscopic analysis and thus are typically detectable only upon activation. As a result, authentic packages incorporating truly latent authenticating agents that are in their latent state can provide the same response to spectroscopic analysis as a package that does not include the authenticating agent.

Particularly preferred authenticating agents include substances for which the second, activated state is a free radical state. Such a state is achievable, for example, by irradiating the authenticating agent with ionizing radiation such as gamma radiation, electron beam radiation, corona discharge, plasma discharge, X-rays, microwave energy, combinations of these, and the like. When so irradiated, authenticating agents in accordance with this embodiment of the present invention form free radicals that can then be spectroscopically analyzed and detected.

Using authenticating agents that have a free radical state as a second, activated state is particularly advantageous because electron spin resonance spectroscopy (ESRS), also known as electron paramagnetic resonance spectros-copy, can be used as a detection method. ESRS is a preferred spectroscopic technique used to detect free radicals which does not rely upon light absorption or reflection to generate a spectroscopic response. As a result, such authenticating agents can be incorporated into any desired portion of any desired goods to be marked, without consideration of optical transparency or transmission capabilities of that portion of the goods. Furthermore, such authenticating agents may be incorporated into, or on the surface of, any layer(s) of packaging material, or may be incorporated anywhere in the product to be packaged, without affecting the detectability of the free radical response.

ESRS is based on the absorption of microwave radiation by a free radical when microwave irradiation occurs in a strong magnetic field. The principles, techniques, and applications of ESRS are widely known and are described, for example, in Alger, *Electron Paramagnetic Resonance: Techniques and Applications* (InterScience, NY, 1968); Ayscough, *Electron Spin Resonance in Chemistry* (Methuen & Co. Ltd. London 1967) and Box, *Radiation Effects. ESR and ENDOR Analysis*, (Academic Press, London N.Y. 1977), the disclosures of which are incorporated by reference herein.

In a typical ESRS system, the source of microwave radiation is a klystron tube. A klystron tube is an electronic oscillator in which a beam of electrons is pulsed between a cathode and a reflector. The klystron tube is typically operated to produce monochromatic radiation having a frequency of about 9500 MHz, the approximate resonance frequency for an unpaired electron. The oscillating output of the klystron tube is transmitted to a waveguide by a loop of wire, which sets up a fluctuating magnetic field (electromagnetic radiation) in the guide. The waveguide, which is commonly a rectangular metal tube, transmits the microwave radiation to the sample which is generally held in a small quartz tube positioned between the poles of a permanent magnet.

Typical settings of an ESR spectrometer include a Klystron frequency of $9.1\times10^9$ Hz, a magnetic field setting of 3240 G or 324 mT, and a field scan range of 20 mT. RF field modulation amplitude, amplification, microwave power, and time constant are adjusted according to the absorbed radiation dose range. For a dose range of 1 kGy/h, for example, suitable settings include a microwave power setting of 4 mW and a field modulation of 100 kHz at 1 mT. Measurements are typically taken at room temperature. The resulting ESR spectra is typically recorded in derivative form to enhance sensitivity and resolution. The resulting spectra may be analyzed by comparison to spectra obtained from reference authentic packages. This comparison may be done either manually or with the aid of, for example, a computer.

Examples of authenticating agents that have a free radical state as a second, activated state include, but are not limited to, amino acids, such as alanine and glutamine; sugars, such as sucrose, lactose, glucose, mannose, maltose, and the like; amine salts (such as methyl amine salts, dimethyl amine salts, trimethyl amine salts and the like) of organic acids, such as amine salts of oxalic acid, malonic acid, succinic acid or glutaric acid; combinations of the foregoing, and the like. Amino acids represent a preferred class of authenticating agents because free radicals of amino acids are relatively stable, biocompatible, easily detected by ESRS, readily available at economic prices, and/or readily purified.

The authenticating agent used in the authentic package, methods and system of the present invention preferably includes one or more isomers of alanine. Alanine is an amino acid having the formula $CH_3C(NH_2)HCOOH$ when in the ground state and forms a stable, detectable free radical (believed to be $CH_3$—CH*—COOH) when exposed to ionizing radiation. The term "alanine" is meant to contemplate all of the various structural and isomeric forms of alanine such as α-alanine, its optical isomers D-alanine, L-alanine, DL-alanine, the linear isomer of alanine, β-alanine, and combinations of these. Alanine is a particularly preferred authenticating agent for several reasons. First, incorporation of amounts of alanine effective to produce detectable amounts of free radicals into typical polymeric packaging materials does not generally substantially alter the mechanical or rheological properties of the polymer used to form the packaging material. Second, isomers of alanine form very stable free radicals. In the case of L-alanine, the half life has been estimated to be as long as 50 years. Furthermore, alanine is generally considered to be biocompatible, being one of the building blocks of DNA and present in the human bloodstream. As a result, its use in food contact applications such as food/beverage packaging is likely to have already received FDA approval or is suitable for FDA approval.

Advantageously, the first, latent state of alanine is also truly latent with respect to ESRS. That is, the latent state of alanine provides a negligible ESR signal, if any at all. Yet, after irradiation, alanine is converted to a free radical that provides a very strong ESR signal. As still another advantage, alanine has a relatively high degradation temperature, e.g., about 300° C., allowing it to be incorporated in products or packaging materials whose manufacture involves temperatures up to about 295° C.

Authenticating agents of the present invention are particularly beneficial when incorporated into a packaging material of a package including a product that is packaged, at least in part, by the packaging material. Preferred packaging materials are flexible, thermoplastic and/or thermosetting films. Such films advantageously are easily conformed substantially to a wide variety of different shapes and surfaces to be packaged. Additionally, many such films are optically transparent, thus allowing potential customers to view the packaged product. Such films can be made by a variety of manufacturing techniques known to the ordinarily skilled artisan including one or more of laminating, blowing, casting, extruding, pressing, molding, coextruding, and the like.

For certain applications, a coextruded, multilayer packaging film which has been oriented, most preferably biaxially oriented, may be preferred. Orienting involves initially cooling an extruded film to a solid state (by, for example, chilled water, air, or other fluid) followed by reheating the film to within its orientation temperature range and stretching it. The stretching step can be accomplished in many ways such as by, for example, blown bubble or tenter framing techniques, both of which are known to those of ordinary skill in the art. After being heated and stretched, the film is quenched rapidly while being maintained in its stretched configuration so as to lock in the oriented molecular configuration. This combination of elongation at elevated temperature followed by cooling causes an alignment of the polymer chains to a more parallel configuration, thereby dramatically altering the mechanical properties of the film. When an unrestrained, unannealed, oriented film subsequently is heated to (or near) its orientation temperature, the film shrinks almost to its original, i.e., pre-elongation dimensions. Such a film is said to be heat shrinkable. For certain end use applications, a film for use as the packaging material in the authentic package, methods and/or system of the present invention preferably can be both biaxially oriented and heat shrinkable.

Oriented films typically are oriented in several directions, usually two directions perpendicular to one another. Orientation in the longitudinal (L) direction is referred to as drawing, whereas orientation in the transverse (T) direction is referred to as stretching. For films extruded through an annular die, stretching occurs when the film is blown to produce a bubble. Thereafter, drawing occurs when the film passes through two sets of powered nip rolls, with the downstream set having a higher surface speed than the upstream set. The resulting draw ratio is the surface speed of the downstream set of nip rolls divided by the surface speed of the upstream set of nip rolls.

Oriented films preferably have a shrink tension of at least about 700 kPa, more preferably at least about 1050 kPa, and most preferably at least about 1400 kPa. Additionally, they can exhibit a Young's modulus (measured in accordance with ASTM D 882) of at least about 100 MPa up to about 1750 MPa. Oriented films generally have a L direction free shrink of at least 1% and a T direction free shrink of at least about 1% (both measured at 85° C.). Where desirable for a particular application, an oriented film can have a free shrink (at 85° C.) in at least one of the L and T directions of at least 2%, at least 5%, at least 10%, at least 15%, at least 20%, at least 25%, even up to 50%. A film can be biaxially oriented and have a free shrink (at 85° C.) in each of the L and T directions of from about 1 to about 20%, more preferably from about 2 to about 15%, and even more preferably from about 3 to about 10%, and a total free shrink (L+T) of from about 2 to about 40%, preferably from about 2.5 to about 30%, more preferably from about 3 to about 20%, and still more preferably from about 5 to about 15%. For certain applications, orienting followed by heat setting or annealing a film so as to provide a T direction free shrink (at 85° C.) of less than 10%, more preferably less than 5%, can be preferred. Heat setting can be accomplished at a temperature from about 60° to 200° C., preferably from about 70° to 150° C., and more preferably from about 80° to 90° C.

A packaging film of the present invention optionally can be subjected to an energetic radiation treatment produced by, for example, corona discharge, plasma, flame, ultraviolet, X-ray, γ-ray, β-ray, or high energy electron systems so as to induce crosslinking between polymer chains. Such irradiative crosslinking of polymeric films is disclosed in, for example, U.S. Pat. No. 4,064,296 (Bornstein et al.), the teaching of which is incorporated herein by reference. Suitable levels of radiation range from about 2 MR to about 15 MR, preferably from about 2 MR to about 10 MR. The desired dosage of radiation can depend on the film composition, thickness, etc., as well as the desired end use of the film. A film used in the package, system and/or methods of the present invention can be used as is, or in connection with irradiated, oriented, heat set films and/or can be laminated, adhesively adhered, extrusion coated, or extrusion laminated onto a substrate to form a laminate. If such an irradiatively crosslinked film is to be included in the package of the present invention, and furthermore, if an authenticating agent that has a free radical state as its second, activated state, is to be included in the film, the crosslinking radiation applied can have the effect of activating at least a portion of the authenticating agent into its second activated state. As is understood by one of ordinary skill in the art, depending on the length of time between the crosslinking irradiation and the spectroscopic analysis and further depending on the half life of the particular authenticating agent selected, a second irradiation specifically for the purpose of activating the authenticating agent may still be carried out if necessary or desired.

Films used in the packaging industry can be categorized according to the number of component layers. Some films are made from a single polymer or blend of polymers and thus have only one layer. However, most commercially available packaging films include more than one layer, i.e., are multilayer films. In general, the layers of a multilayer film can be classified as inner or outer. Additionally, any number of tie layers can be included. Where a film for use in the present invention is shrinkable, it preferably includes up to about 20 layers, more preferably 3 to about 12 layers (especially where the total number of layers is an odd number), although any number of layers are feasible as long as the film provides the desired properties for the particular packaging operation in which it is to be used. Regardless of the particular number or order of the film layers, those films with at least one layer that includes a polymer including mer units derived from ethylene are useful for many end use applications. Advantageously, the authenticating agent of the present invention may be incorporated into any one or more of the multiple layers, as the location of the authenticating agent within the package is not critical inasmuch as the authenticating agent may be activated and detected from any position in or on the film.

When the packaging material used in the package, method and system of the present invention is a multilayer film, it can include those films that have one or more of the following types of layers: abuse layers, barrier layers, tie layers, bulk layers, and seal layers. The physical properties required of a film for any given end use application often determine the composition of the film and/or the compositions of the various layers of the film. Where a variety of properties are required, a variety of layers containing differing polymeric components can be, and usually are, employed.

For example, if the product(s) being packaged is/are desirably protected from one or more detrimental materials (e.g., atmospheric $O_2$), a barrier layer including, for example, ethylene/vinyl alcohol interpolymer (EVOH), vinylidene chloride interpolymer, or one or more of certain polyamides (e.g., nylons) can be included in the multilayer film structure. If the barrier layer employed is one including a material known to be sensitive to moisture, such as EVOH, and the application requires exposure of the film to moisture, then one or more moisture barrier layers also can be included. If the film is likely to be subjected to abuse during handling and/or transport, an abuse layer can be provided (either as an inner or outer layer). One or two seal layers can be provided to allow for sealing of the film to itself or another packaging article during the formation of a package. One or more inner layers also can be provided, and films with at least one inner layer are preferred for many applications.

When a flexible film is a multilayer film, those films containing at least one layer including a polymer that includes mer units derived from ethylene can be preferred for some end use applications. These polymers can be ethylene homopolymers or they also can include mer units derived from one or more of (meth)acrylic acid, a $C_3$–$C_{20}$ α-olefin, $C_1$–$C_{20}$ esters of (meth)acrylic acid, vinyl acetate, and vinyl alcohol. Ionomers also can be useful. Particularly preferred for many applications are ethylene/α-olefin interpolymers.

The relatively recent advent of single site-type catalysts (e.g., metallocenes) necessitates further definitional clarification when discussing ethylene homo- and copolymers. Heterogeneous polymers are those having relatively wide variation in molecular weight and composition distribution. Polymers prepared with, for example, conventional Ziegler Natta catalysts are heterogeneous. Such polymers can be used in a variety of layers including the seal layer(s). On the other hand, homogeneous polymers have relatively narrow molecular weight and composition distribution. Homogeneous polymers differ structurally from heterogeneous polymers in that they exhibit a relatively even sequencing of comonomers within a chain, a mirroring of sequence distribution in all chains, and a similarity of chain lengths, i.e., a narrower molecular weight distribution. Homogeneous polymers typically are prepared using metallocene or other single site-type catalysts. Homogeneous polymers also can be used in a variety of layers including the seal layer(s).

The term "ethylene/α-olefin copolymer" (or interpolymer) as used herein refers both to heterogeneous materials such as LDPE, medium density polyethylene (MDPE), linear low density polyethylene (LLDPE), and very low and ultra low density polyethylene (VLDPE and ULDPE), as well as to homogeneous materials which, in general, are prepared by the copolymerization of ethylene and one or more α-olefins. The comonomer preferably is a $C_4$–$C_{20}$ α-olefin, more preferably a $C_4$–$C_{12}$ α-olefin, still more preferably a $C_4$–$C_8$ α-olefin. Particularly preferred α-olefins include 1-butene, 1-hexene, 1-octene, and mixtures thereof. In general, from about 80 weight percent to about 99 weight percent ethylene and from about 1 to about 20 weight percent α-olefin, preferably from about 85 weight percent to about 95 weight percent ethylene and from about 5 weight percent to about 15 weight percent α-olefin, a copolymerized in the presence of a single site catalyst. Examples of commercially available homogeneous materials include the metallocene catalyzed Exact™ resins (Exxon Chemical Co.; Baytown, Tex.), substantially linear Affinity™ and Engage™ resins (Dow Chemical Co.; Midland, Mich.), and Tafiner™ linear resins (Mitsui Petrochemical Corp.; Tokyo, Japan).

Homogeneous ethylene/α-olefin copolymers can be characterized by one or more methods known to those of skill in the art, such as molecular weight distribution ($M_w/M_n$), composition distribution breadth index (CDBI), narrow melting point range, and single melt point behavior. Molecular weight distribution, also known as polydispersity, can be determined by, for example, gel permeation chromatography. Homogeneous ethylene/α-olefin copolymers to be used in a layer of the film of the present invention preferably have an $M_w/M_n$ of less than 2.7; more preferably from about 1.9 to about 2.5; still more preferably, from about 1.9 to about 2.3.

The CDBI of homogeneous ethylene/α-olefin copolymers generally is greater than about 70%. CDBI is defined as the weight percent of copolymer molecules having a comonomer content within 50%, i.e., ±50% of the median total molar comonomer content. CDBI can be determined by temperature rising elution fractionation as described by, for example, Wild et al., *J. Poly. Sci.—Poly. Phys. Ed.*, vol. 20, 441 (1982). Linear polyethylene, which does not contain a comonomer, is defined to have a CDBI of 100%. CDBI determination clearly distinguishes homogeneous copolymers (CDBI values generally above 70%) from presently available VLDPEs (CDBI values generally less than 55%).

Homogeneous ethylene/α-olefin copolymers also typically exhibit an essentially single melting point with a peak melting point ($T_m$), as determined by differential scanning calorimetry (DSC), of from about 60° to 105° C., more precisely a peak $T_m$ of from about 80° to 100° C. As used herein, the phrase "essentially single melting point" means that at least about 80% (by weight) of the material corresponds to a single $T_m$ at a temperature within the range of from about 60° to about 105° C., and essentially no substantial fraction of the material has a peak melting point in excess of about 115° C. as determined by DSC analysis (e.g., on a Perkin Elmer™ System 7 Thermal Analysis System). The presence of higher melting peaks has been found to be detrimental to film properties such as haze and seal initiation temperature.

Of course, additives commonly included in thermoplastic or thermosetting films also can be included in a film used in the package, methods and/or system of the present invention. Typical additives include antislip agents, antiblocking agents (particularly diatomaceous earth and alkali aluminosilicate ceramic microspheres), antifogging agents, reinforcements, fillers, extenders, pigments, lubricants, antioxidants, heat stabilizers and the like.

Where the packaging material to be used in the package of the present invention is a flexible film, it can take the form of a stretch film, a film suitable for vertical or horizontal form-fill-and-seal end use, a lidstock film, a film suitable for vacuum skin packaging, a film suitable for use as a barrier bag, a film suitable for use as a patch bag, a film suitable for use in case ready packaging, a film suitable for use in a thermoformed container (particularly in a film used as a liner in a thermoformed tray, such as a polystyrene tray), an aroma/odor barrier film, a film suitable for use in cook-in end use applications (especially heat shrinkable bags, heat shrinkable and non-heat shrinkable casings, and containers thermoformed from non-heat shrinkable films and sheets), and/or a medical film. Some specific examples of such flexible films include:

(a) films used to produce bags such as those described in, for example, U.S. Pat. No. 3,741,253 (Brax et al.), U.S. Pat. No. 3,891,008 (D'Entremont), U.S. Pat. No. 4,048,428 (Baird), and U.S. Pat. No. 4,284,458 (Schirmer);

(b) films used to produce bags for cook-in applications, such as those described in, for example, U.S. Pat. Nos. 4,064,296 (Bornstein et al.) and U.S. Pat. No. 4,855,183 (Oberle);

(c) films used in connection with patch bags, such as those described in, for example, U.S. Pat. No. 4,755,403 (Ferguson), (d) shrink films such as those described in, for example, U.S. Pat. Nos. 4,551,380 and 4,643,943 (both to Schoenberg);

(e) films having oxygen, moisture, or odor barrier functionality such as those described in, for example, U.S. Pat. No. 4,064,296 (Bornstein et al.), U.S. Pat. No. 4,724,185 (Shah), U.S. Pat. No. 4,839,235 (Shah), and U.S. Pat. No. 5,004,647 (Shah);

(f) films suitable for medical applications such as, for example, those described in U.S. Pat. No. 5,695,840 (both to Mueller);

(g) films suitable for use in a thermoformed package such as, for example, those disclosed in U.S. Pat. No. 4,735,855 (Wofford et al.);

(h) stretch/shrink-type films such as those disclosed in, for example, U.S. Pat. No. 4,617,241 (Mueller);

(i) films suitable for the packaging of flowable or pumpable products such as those disclosed in, for example, U.S. Pat. No. 4,746,562 (Fant);

(j) films suitable for packaging, water cooking, and storing food products such as are disclosed in, for example, U.S. Pat. No. 4,104,404 (Bieler et al.);

(k) hot blown films of a type useful in chub packaging such as are described in, for example, U.S. Pat. No. 4,937,112 (Schirmer);

(l) films having LLDPE or LMDPE in a core and/or an intermediate layer, such as those described in, for example, U.S. Pat. No. 4,532,189 (Mueller) U.S. Pat. No. 4,194,039 (Mueller), U.S. Pat. No. 4,390,385 (Ferguson et al.), U.S. Pat. No. 4,274,900 (Mueller et al.), U.S. Pat. No. 4,188,443 (Mueller et al.), and U.S. Pat. No. 5,298,302 (Boice);

(m) films having a low shrink energy such as those disclosed in, for example, U.S. Pat. No. 4,833,024 (Mueller) and U.S. Pat. No. 5,023,143 (Nelson);

(n) films suitable for use in vacuum skin packaging applications, such as those disclosed in, for example, U.S. Pat. No. 4,886,690 (Davis et al.), U.S. Pat. No. 4,963,427 (Botto et al.), and U.S. Pat. No. 5,075,143 (Bekele);

(o) films including one or more layers that contain a homogeneous polymer such as those disclosed in, for example, European Publication No. 0 597 502 A3 (Babrowicz et al.) as well as U.S. Pat. No. 5,604,043 (Ahlgren) and U.S. Pat. No. 5,491,019 (Kuo); and (p) films having high oxygen transmission rates such as, for example, those described in U.S. Pat. No. 5,491,019

(Kuo) and U.S. Pat. No. 5,523,136 (Fischer et al.) as well as U.S. patent application Ser. No. 08/889,000 (Mossbrook et al.).

The teachings of each of the foregoing references are incorporated herein by reference. Those of ordinary skill in the art can envision other types of films and/or other materials which would be useful as the packaging material in the authentic package, methods and/or system of the present invention; these too are within the scope of the present invention.

The manner in which the authenticating agent(s) is/are incorporated into items to be marked, such as packaging material, is not critical and, thus, can vary extensively. For example, where the packaging material is paperboard, standard blending, printing, and/or overcoating techniques can be used. Where the item is polymeric, such as a flexible polymeric packaging film, blending with a polymer melt or solids mixing of the authenticating agent with a polymeric powder are preferred incorporation techniques, although printing and/or overcoating techniques also can be used. For concrete, mortar, cement, plaster, or the like, the agent can be blended into the mixture before it cures. Those of ordinary skill in the art are familiar with these and other similar or substantially identical techniques.

In certain embodiments of the present invention, the authenticating agent may desirably be incorporated into the product. The manner of incorporation of the authenticating agent into the desired product is not critical, and thus, may be accomplished in a wide variety of ways. As above, the authenticating agent may be incorporated into the product by overcoating, blending, printing, and the like. Furthermore, the identity of the goods to be marked for authenticity is relatively unimportant. Any goods that are susceptible to copying or counterfeiting, or the source of which needs to be confirmed, can benefit from the authentication methods or system of the present invention. Examples include, but are not limited to compact discs, perfumes, official documents, medical instruments, bottle cap liners, tires, windshields, official documents, flexible packaging films, rigid packaging containers, textiles, food items, inks, toners, fasteners, piping, plumbing fixtures, aircraft parts, motor vehicle parts, train parts, watercraft parts, building construction components, adhesives, cleaners, engine components, paint, varnish, manufactured boards, caulk, flooring, mortar, insulation, expanded foam, cement, concrete, joint compound, tar, drywall, and the like.

Some crystalline or other solid substances suitable for use as authenticating agents tend to yield more isotropic ESRS signals when utilized as relatively smaller particles. Thus, if such a substance (alanine is a good example of such a substance) is chosen for use as the authenticating agent, the authenticating agent preferably is ground into particles of a size which is as fine as possible prior to incorporation into the authentic package. For example, smaller sized alanine particles generally yield more isotropic ESR signals and thus, if alanine is to be utilized as the authenticating agent, the alanine particles are preferably ground to a diameter of about 10 $\mu$m or less, more preferably about 5 $\mu$m or less, prior to incorporation into the product(s) and/or packaging material(s) of a package in accordance with the present invention. Particle diameter can be determined by a MasterSizer™ light scattering instrument (Malvern Instruments; United Kingdom).

Any conventional grinding or milling technique may be used to reduce the diameter of the authenticating agent particles. Preferably, the diameter of the authenticating agent particles is reduced by jet milling. Jet milling with a Micro-jet™ Fluid Energy Mill apparatus (Aljet Division, Fluid Energy Processing and Equipment Co.; Plumsteadville, Pa.), for example, has provided ground alanine with a particle size of about 5 $\mu$m.

The authenticating agent may be incorporated into a product and/or packaging material in any amount effective to provide a detectable spectroscopic response. The amount of authenticating agent relative to the amount of the material of the product or packaging material preferably is not so high that the properties of the product or packaging are unduly compromised. However, the package of the present invention desirably contains enough of the authenticating agent relative to the product or packaging material so as to be detectable by spectroscopic means when the authenticating agent is in its second, activated state. As general guidelines, bearing these considerations in mind, the authenticating agent may be incorporated into the product or packaging material in amounts of from about 0.001 ppm to about 95 weight percent of authenticating agent relative to the total weight of the product or packaging material. As one specific example, when the authenticating agent includes alanine and is to be incorporated into a polymeric packaging material, from about 10 ppm to about 30 weight percent, preferably from about 50 ppm to about 10 weight percent, more preferably from about 100 ppm to about 5 weight percent, has been found to be suitable.

As one specific example of an approach for preparing a composition in accordance with the present invention wherein the authenticating agent is incorporated into a flexible film packaging material by a blending technique, the authenticating agent and the material(s) selected for use as the packaging material first can be admixed until a substantially homogeneous mixture results. Such mixing can take place at room temperature or at an elevated temperature depending on the nature of the selected materials. Furthermore, the authenticating agent and material(s) may be mixed together manually or by mechanical means, such as a roll mill. Once a substantially homogeneous mixture has been formed, the mixture can be extruded, flow coated, pressed, blow molded, or otherwise processed to form a packaging film or layer of such a film of the desired dimensions and structure.

The particular parameters of each fabrication technique can depend on the particular packaging material and authenticating agent chosen. More specifically, the parameter chosen should be effective to allow formation of a film layer of the desired dimensions while not adversely affecting the properties of the authenticating agent.

Once such a packaging material and/or product incorporating an authenticating agent in accordance with the present invention has been produced, a package of the present invention can be formed by wrapping or enclosing the product in at least the packaging material, the mechanics of which depend on the nature of the packaging material and of the product. Such packaging may occur, for example, by placing a product in a paperboard container that has been coated with the authenticating agent; a product incorporating an authenticating agent may be placed in such a paperboard container, a product may be placed into a paperboard container, which container is subsequently shrink wrapped in a packaging film comprising an authenticating agent; and the like.

A package in accordance with the present invention may have its authenticity verified, or alternatively, an unknown item may have its source or authenticity verified, readily and easily utilizing the method and system of the present invention.

At a desired time, an item can first be subjected to a treatment effective to stimulate at least a portion of an authenticating agent incorporated therein, if present, to the second, activated state of the authenticating agent. Once an item has been irradiated, the item thereafter can be subjected to a spectroscopic analysis capable of detecting free radicals. The spectral response of the item then can be compared to a reference spectroscopic response of an irradiated, authentic item. If the two spectroscopic response do not match, the item is not authentic, i.e., it is counterfeit or the goods of another.

The present invention will now be further described with reference to the following examples.

EXAMPLES

Example 1

Commercially available L-alanine powder was ground to a mean particle size of roughly 5 μm using a Microjet™ Fluid Energy mill and 1 g of the milled L-alanine was added to 99 g of Poly-Eth™ 1017 LDPE resin (Chevron Corp; San Ramon, Calif.). This mixture was pulverized in a Certiprep™ 6750-115 freezer mill (SPEX, Inc; Metuchen, N.J.) in a liquid $N_2$ atmosphere at approximately −90° C.

The resulting powder was melted and pressed into a film having a thickness of several mils using a Model C Carver Laboratory press (Fred C. Carver, Inc; Menomonee Falls, Wis.). A control film was also prepared in the same manner, but with a composition of 100% LDPE (i.e., no alanine). Both films were irradiated with electron beam radiation under controlled conditions of amperage and exposure time to deliver to a nominal dose of 73 kGy, to activate the alanine. These conditions had previously been calibrated against standards in collaboration with the National Institute of Standards and Technology (Gaithersburg, Md.).

Figure 1B:
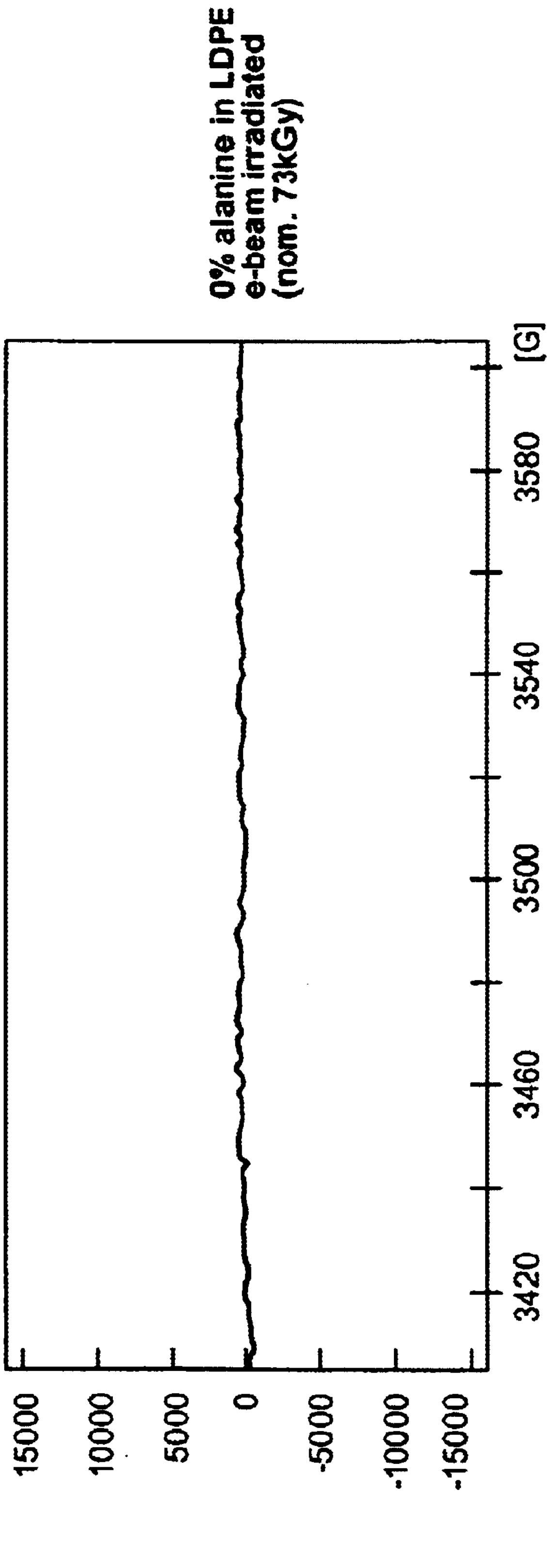
FIG. 1B is an electron spin resonance spectrum of an LDPE film that does not include L-alanine, but that has been exposed to electron beam irradiation at a dose of 73 kGy.
Figure 1C:
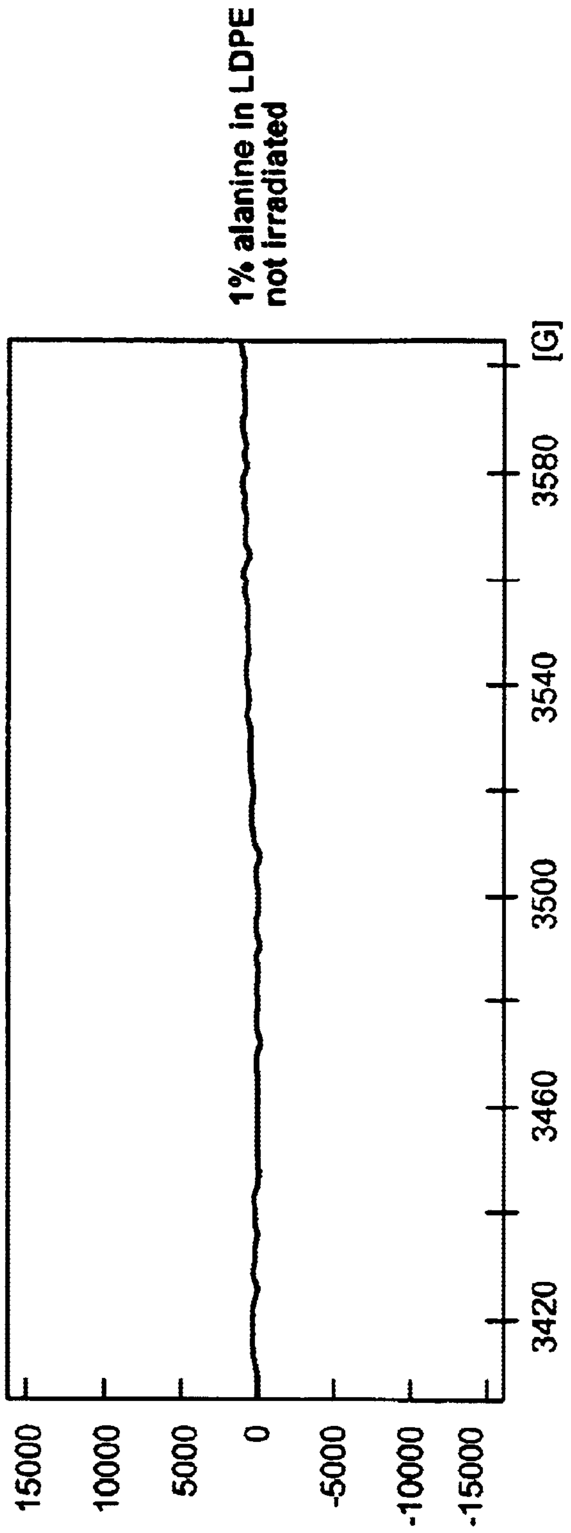
FIG. 1C is an electron spin resonance spectrum of an LDPE film including 1% L-alanine that has not been exposed to ionizing irradiation.
Figure 2:
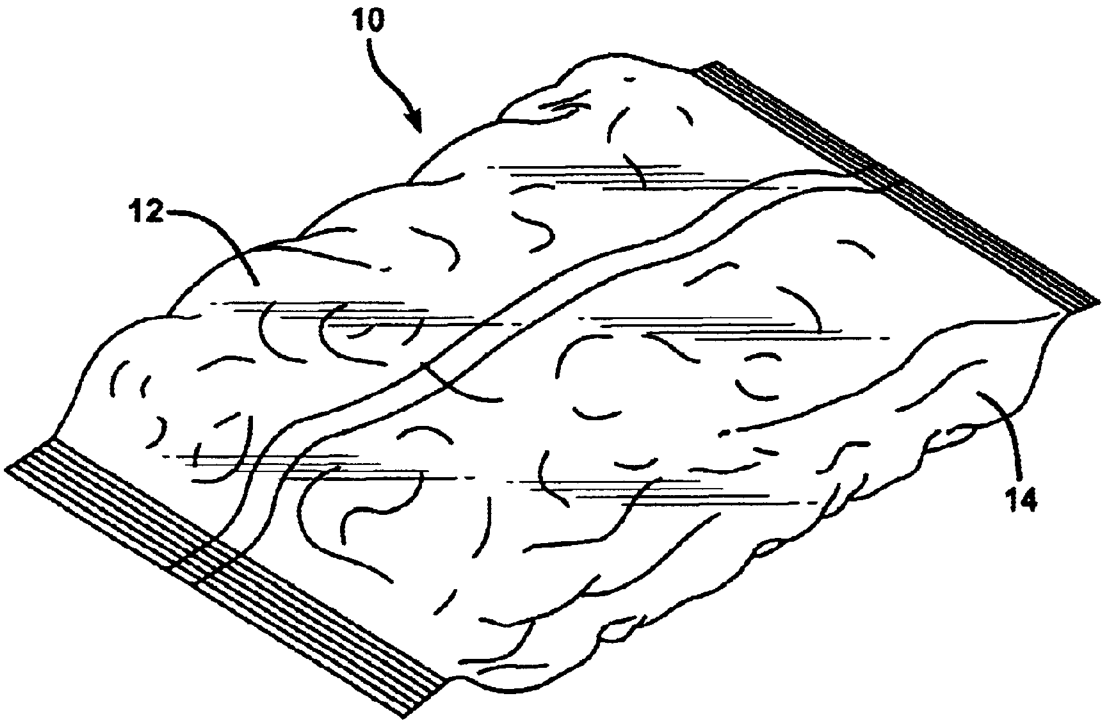
FIG. 2 is a perspective view of a package 10 according to the present invention comprising a product 12 and a packaging polymeric film 14 incorporating an authenticating agent.
Figure 3:
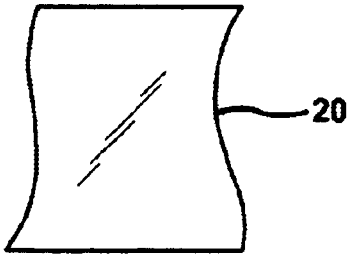
FIG. 3 is a representational plan view of the representative reference example 20 for the polymeric film 14 of FIG. 2.
Figure 4:
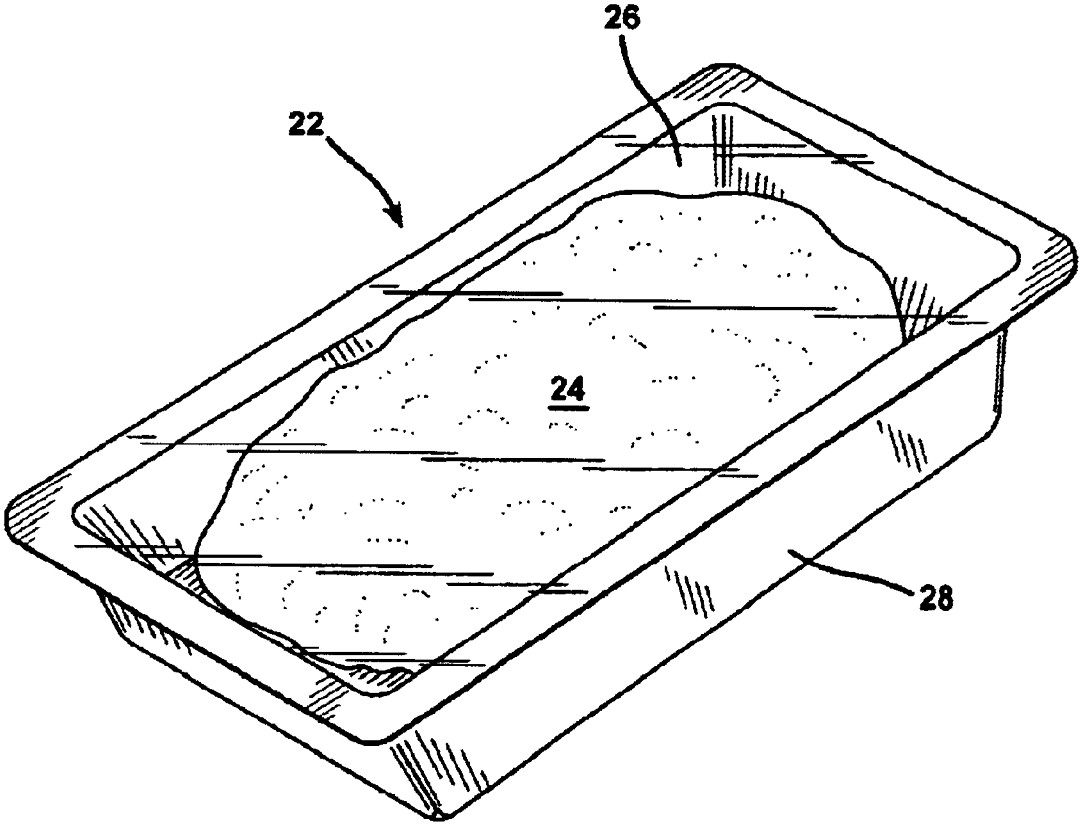
FIG. 4 is a perspective view of a package 22 according to the present invention comprising a product 24, a polymeric lid 26, and a tray 28 incorporating an authenticating agent and comprising a substance selected from paperboard, chipboard, and cardboard.

Both films were analyzed before and after irradiation via ESRS on a model ECS 106ESR spectrometer equipped with a TMH Cavity (Bruker Instruments Inc; Billerica, Mass.). Conditions for the ESRS analysis included a modulation amplitude of 16 G, a conversion time of 40.96 ms, a time constant of 2.6 s, a sweep time of 42 s, a sweep width of 18 G and at a microwave power of 10 mW. Relevant and illustrative ESR data are given in FIGS. 1A, 1B, and 1C. The irradiated film known to contain L-alanine gave the unique and characteristic signal indicative of the presence of an amount of alanine free radical as shown in FIG. 1A. The control film failed to produce any spectral response after irradiation as shown in FIG. 1B. FIG. 1C shows the ESR signal obtained from the film containing L-alanine before irradiation. No spectral response is detected in FIG. 1C, thereby demonstrating that alanine does not provide a spectral response until activated by irradiation.

Example 2

100 ppm of L-alanine was added to a bottle cap liner formulation including 70% LLDPE, 15% ethylene/propylene copolymer, 7% ethylene/propylene rubber and 8% mineral oil. Prior to blending, commercially available L-alanine powder was ground to a mean particle size of roughly 5 μm as described in Example 1. The alanine modified formulation was blended directly in a single screw laboratory extruder (Baker Perkins Chemical Machinery; Stoke-on-Trent, UK), pelletized and cold molded into a standard 28 mm diameter polypropylene bottle cap to form a sealing liner inside the cap. During compounding, the extruder temperature was maintained between 120° C. and 140° C. Control liners were prepared in the same manner with the exception that L-alanine was not added to the bottle cap liner formulation.

Two control and two test bottle caps, complete with liners, were irradiated with γ radiation at a dose of 25.7 kGy to activate the L-alanine, if any, to a detectable free radical state. The irradiations were performed in a GammaCell™ 232 (MDS Nordion; Toronto) cobalt source at a dose rate of 9.3 kGy/hr. The temperature during irradiation was 23° C.

The lines were then removed substantially intact from the control and test bottle caps. These bottle cap liners were then analyzed via ESRS as in Example 1. The analyst performing the ESRS analysis did not know which liners were test liners and which were control liners.

ESRS data analogous to that shown in FIGS. 1A, 1B, and 1C was obtained and the test and control liners could be readily differentiated by their respective ESRS responses. Specifically, the test liners showed a strong ESRS signal analogous to FIG. 1A. The control liners showed substantially no ESRS response analogous to FIG. 1B or FIG. 1C.

Example 3

Portland cement, sand and water were mixed to form a slurry. To this slurry was added 100 ppm of L-alanine based on the dry weight of the slurry. The resulting mortar mixture including alanine was allowed to harden at room temperature over seven days in a 100% humidity controlled environment. A control mortar sample was also prepared in the same manner but without L-alanine. Once the tests and control mortar samples had hardened, they were irradiated with γ radiation at a dose of 234 kGy to activate the L-alanine, if any, to a detectable free radical state. The irradiations were performed as in Example 2.

These samples were analyzed via ESRS as described in Example 1. The analyst performing the ESRS analysis did not know which cement sample was a test sample and which was a control sample. ESRS data analogous to that shown in FIGS. 1A, 1B, and 1C was obtained and the test and control mortar samples were readily differentiable. Specifically, the irradiated cement including alanine provided an ESRS response analogous to FIG. 1A. The irradiated mortar lacking alanine provided substantially no ESRS response analogous to FIGS. 1B and 1C.

Example 4

Affinity™ PF1140 homogeneous polyethylene resin (Dow Chemical Co.) was blended with L-alanine to form a masterbatch resin. Prior to blending, commercially available L-alanine powder was ground to a mean particle size of roughly 5 μm as in Example 1. Sufficient alanine was added to the masterbatch blend so that the total concentration of alanine in the final coextruded film, described below, was nominally 1000 ppm.

This masterbatch blend was coextruded with a variety of other commercially available resins to form a 9-layer film. These resins included a Affinity™ PL1850 polyethylene resin (Dow Chemical Co.), Escorene™ PD-9302 ethylene/propylene copolymer containing a 3% ethylene (Exxon Chemical Co.), Eval™ LC E151A ethylene/vinyl alcohol copolymer containing 44% vinyl alcohol (Evalca; Pasadena, Tex.), Elvax™, 3165, ethylene/vinyl acetate copolymer containing 18% vinyl acetate (E.I. Dupont de Nemours & Co.; Wilmington, Del.), Surlyn™ 16010 ionomer resin (Dupont), Fortiflex™ J60-500 high density polyethylene (Solvay, Advanced Polymers, Inc.; Houston, Tex.), Bynel™ E302 anhydride grafted polypropylene (Dupont), and Bynel™ CXA 3062 anhydride grafted ethylene/vinyl acetate copolymer containing 16% vinyl acetate (Dupont). The resins were coextruded in a manner such that the alanine containing masterbatch blend formed an inner layer and accounted for approximately 35% of the total film weight. The final film thickness was $6.6\times10^3$ $\mu$m. A control multilayer film was prepared in the same manner with the exception that no L-alanine was added.

The test and control multilayer films were irradiated with electron beam radiation under controlled conditions of amperage and exposure time to deliver a nominal dose of 100 kGy, to activate the alanine. These conditions had previously been calibrated against standards in collaboration with NIST. These films were then analyzed via ESRS as in Example 1. The analyst performing the ESRS analysis did not know which films were control and which were test films. ESRS data analogous to that shown in FIGS. 1A, 1B and 1C was obtained and the test and control films were readily differentiable. Specifically, the irradiated film including alanine provided an ESRS response analogous to FIG. 1A. The irradiated film lacking alanine provided substantially no ESR response analogous to FIGS. 1B and 1C.

What is claimed is:

1. A package comprising:

a product; and one or more packaging materials enclosing the product, wherein an effective amount of authenticating agent is incorporated into the one or more packaging materials and wherein the authenticating agent is a substance that forms detectable free radicals upon irradiation.

2. The package of claim 1, wherein the one or more packaging materials comprises a polymeric packaging film, said authenticating agent being incorporated in said film.

3. The package of claim 1, wherein the authenticating agent comprises at least one of an amino acid, a sugar, and an amine salt of an organic acid.

4. The package of claim 3, wherein the authenticating agent comprises alanine.

5. The package of claim 1, wherein the product comprises at least one of a food product and a beverage product.

6. A method of making a package, comprising:

incorporating an authenticating agent into a packaging material as an in situ product marker; and forming a package comprising the the packaging material, wherein the authenticating agent is a substance that forms detectable free radicals when exposed to ionizing radiation, said authenticating agent being present in a manner such that the free radicals provide a characteristic spectral response when subjected to a spectroscopic analysis capable of detecting free radicals in order to allow authentication of the package from said spectral response.

7. The method of claim 6, wherein the packaging material comprises a polymeric packaging film, and wherein the authenticating agent is incorporated into said film.

8. The method of claim 6, wherein the authenticating agent comprises alanine.

9. A method of authenticating a package comprising:

providing a package incorporating a given amount of one or more authenticating agents that upon exposure to a given effective dosage of radiation is capable of forming detectable free radicals having a characteristic spectral response;

exposing at least a portion of a package to be authenticated to the given effective dosage of radiation;

spectroscopically analyzing the irradiated package portion to obtain a spectral response for the irradiated package portion; and comparing the spectral response for the irradiated package portion to the characteristic spectral response to determine whether the package to be authenticated is authentic.

10. The method of claim 9, wherein the spectroscopically analyzing comprises electron spin resonance spectroscopy.

11. The method of claim 9, wherein the given effective amount of radiation comprises at least one of gamma radiation, electron beam radiation, corona discharge, plasma discharge, X-rays and microwave energy.

12. The method of claim 9, wherein at least one of the one or more authenticating agents comprises alanine.

13. A method of authenticating a package comprising:

providing a package incorporating a given amount of one or more authenticating agents that upon exposure to a given effective dosage of radiation is capable of forming detectable free radicals having a characteristic spectral response;

exposing a representative reference example of the package incorporating the authenticating agent to the given effective amount of radiation;

spectroscopically analyzing the irradiated representative reference example to obtain the characteristic a spectral response for the irradiated representative reference example;

exposing at least a portion of a package to be authenticated to the given effective dosage of radiation;

spectroscopically analyzing the irradiated package portion to obtain a spectral response for the irradiated package portion; and comparing the spectral response for the irradiated package portion to the characteristic spectral response for the irradiated representative reference example to determine whether the package to be authenticated is authentic.

14. The method of claim 13, wherein the given effective amount of radiation comprises at least one of gamma radiation, electron beam radiation, corona discharge, plasma discharge, X-rays and microwave energy.

15. The method of claim 13, wherein the spectroscopically analyzing comprises electron spin resonance spectroscopy.

16. The method of claim 13, wherein at least one of the one or more authenticating agents comprises at least one of an amino acid, a sugar, and an amine salt of an organic acid.

17. The method of claim 13, wherein at least one of the one or more authenticating agents comprises alanine.

18. The method of claim 13 wherein at least one of the one or more authenticating agents comprises an amino acid.

19. The method of claim 13 wherein at least one of the one or more authenticating agents comprises a sugar.

20. The method of claim 13 wherein at least one of the one or more authenticating agents comprises an amine salt of an organic acid.

21. The method of claim 13 wherein the package comprises a food product, and the one or more authenticating agents are incorporated in the food product.

22. The method of claim 13 wherein the package comprises a polymeric film having at least one layer comprising ethylene homopolymer and at least one of the one or more authenticating agents is incorporated in the at least one layer.

23. The method of claim 13 wherein the package comprises a polymeric film having at least one layer comprising ethylene/$C_3$–$C_{20}$ alph-olefin copolymer and at least one of the one or more authenticating agents is incorporated in the at least one layer.

24. The method of claim 13 wherein the package comprises a polymeric film having at least one layer comprising ethylene/vinyl alcohol copolymer and at least one of the one or more authenticating agents is incorporated in the at least one layer.

25. The method of claim 13 wherein the package comprises a polymeric film having at least one layer comprising ethylene/(meth)acrylic acid copolymer and at least one of the one or more authenticating agents is incorporated in the at least one layer.

26. The method of claim 13 wherein the package comprises a polymeric film having at least one layer comprising ethylene/$C_1$–$C_{20}$ ester of (meth)acrylic acid copolymer and at least one of the one or more authenticating agents is incorporated in the at least one layer.

27. The method of claim 13 wherein the package comprises a polymeric film having at least one layer comprising ethylene/vinyl acetate copolymer and at least one of the one or more authenticating agents is incorporated in the at least one layer.

28. The method of claim 13 wherein the package comprises a polymeric film having at least one layer comprising polyamide and at least one of the one or more authenticating agents is incorporated in the at least one layer.

29. The method of claim 13, wherein the package comprises a polymeric film having at least one layer comprising ionomer and at least one of the one or more authenticating agents is incorporated in the at least one layer.

30. The method of claim 13, wherein the package comprises a substance selected from the group consisting of paperboard, chipboard, and cardboard, and at least one of the one or more authenticating agents is incorporated in the substance.

31. The method of claim 13 wherein the package comprises a packaging material and the one or more authenticating agents are present in an amount ranging from about 100 ppm to about 5 weight percent based on the weight of the packaging material.

32. The method of claim 13 wherein the package comprises a hot blown film and at least one of the one or more authenticating agents is incorporated in the hot blown film.

* * * * *

UNITED STATES PATENT AND TRADEMARK OFFICE

CERTIFICATE OF CORRECTION

PATENT NO. : 6,806,478 B1
DATED : October 19, 2004
INVENTOR(S) : Hatfield

It is certified that error appears in the above-identified patent and that said Letters Patent is hereby corrected as shown below:

Column 19,
Line 1, "alph" should be -- alpha --.

Signed and Sealed this

Twenty-sixth Day of April, 2005

JON W. DUDAS
*Director of the United States Patent and Trademark Office*